United States Patent [19]
Janusz et al.

[11] Patent Number: 6,110,960
[45] Date of Patent: Aug. 29, 2000

[54] DIHYDROBENZOPYRAN AND RELATED COMPOUNDS USEFUL AS ANTI-INFLAMMATORY AGENTS

[75] Inventors: John Michael Janusz, West Chester, Ohio; Carl Randolph Johnson; Chandrawansha Bandara Weerasinghe Senanayake, both of Detroit, Mich.

[73] Assignee: The Procter & Gamble Company, Cincinnati, Ohio

[21] Appl. No.: 09/194,962

[22] PCT Filed: Jun. 6, 1997

[86] PCT No.: PCT/US97/09945
  § 371 Date: Dec. 7, 1998
  § 102(e) Date: Dec. 7, 1998

[87] PCT Pub. No.: WO97/46548
  PCT Pub. Date: Dec. 11, 1997

Related U.S. Application Data

[60] Provisional application No. 60/019,414, Jun. 7, 1996.

[51] Int. Cl.⁷ .......................... A61K 31/38; A61K 31/35; C07D 335/04; C07D 311/04
[52] U.S. Cl. .......................... 514/432; 514/456; 549/23; 549/405
[58] Field of Search .......................... 549/23, 405; 514/432, 514/456

[56] References Cited

U.S. PATENT DOCUMENTS

| | | | |
|---|---|---|---|
| 4,341,792 | 7/1982 | Barnish et al. | 424/275 |
| 4,545,993 | 10/1985 | Okamoto et al. | 514/456 |
| 4,680,404 | 7/1987 | Eggler et al. | 546/269 |
| 4,829,080 | 5/1989 | Maignan et al. | 514/432 |
| 5,480,858 | 1/1996 | Sakamoto et al. | 504/288 |
| 5,675,024 | 10/1997 | Teng et al. | 549/405 |
| 5,837,725 | 11/1998 | Dawson et al. | 514/467 |
| 5,912,244 | 6/1999 | MacKenzie et al. | 514/247 |
| 5,919,817 | 7/1999 | Jacobsen et al. | 514/456 |

FOREIGN PATENT DOCUMENTS

WO 97/46548   12/1997   WIPO .

*Primary Examiner*—Deborah C. Lambkin
*Attorney, Agent, or Firm*—Mary Pat McMahon; Carl J. Roof; David L. Suter

[57] ABSTRACT

A compound having structure (1) wherein (a) X is selected from the group consisting of O, S, SO, or $SO_2$; (b) each Y is independently hydrogen or straight, branched or cyclic alkanyl having from 1 to about 4 carbon atoms, or the two Y's are bonded to form an alkanyl ring having from 3 to about 7 carbon atoms; (c) Z is branched or cyclic alkyl having from 3 to about 10 atoms other than hydrogen; (d) W is O or S; and (e) R is straight, branched or cyclic alkyl or aryl, saturated or mono- or di-unsaturated with double or triple bonds, R having from 1 to about 15 atoms other than hydrogen; pharmaceutical compositions comprising such compounds, and methods of treating inflammation or pain using such compounds.

(I)

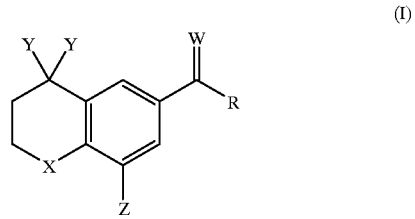

18 Claims, No Drawings

DIHYDROBENZOPYRAN AND RELATED COMPOUNDS USEFUL AS ANTI-INFLAMMATORY AGENTS

Provisional Application No. 60/019,414 filed Jun. 7, 1996, this application is a 371 of PCT/US97/09945 filed Jun. 6, 1997.

TECHNICAL FIELD

The subject invention relates to nonsteroidal anti-inflammatory drugs, particularly to substituted dihydrobenzopyran and related compounds.

BACKGROUND OF THE INVENTION

Certain dihydrobenzopyran compounds and other compounds structurally related thereto have been found to have significant disease altering activities. Such compounds, processes for making them, and uses for them are disclosed in the following references: Bernardon, Jean-Michel, Biaromatic propynyl compounds, pharmaceutical compositions and cosmetics containing them, and their uses. EP 661258 Al 950705; Yoshimura, Hiroyuki; Nagai, Mitsuo; Hibi, Shigeki; Kikuchi, Kouichi; Abe, Shinya; Hida, Takayuki: Higashi, Seiko; Hishinuma, Ieharu; Yamanaka, Takashi, A Novel Type of Retinoic Acid Receptor Antagonist: Synthesis and Structure-Activity Relationships of Heterocyclic Ring-Containing Benzoic Acid Derivatives. J. Med. Chem. (1995), 38(16), 3163–73; Yoshimura, Hiroyuki; Nagai, Mitsuo; Hibi, Shigeki: Kikuchi, Koichi; Hishinuma, Ieharu; Nagakawa, Junichi; Asada, Makoto; Miyamoto; Norimasa; Hida, Takayuki; et al. Heterocyclic carboxylic acid derivatives which bind to retinoid receptors (RAR). WO 9414777 A1 940707; Klaus, Michael; Mohr, Peter, Preparation and formulation of benzothiepins, -thiopyrans, and -thiophenes as immunomodulators. EP 568898 A1 9311 10; Bernardon, Jean Michel, Preparation and formulation of 4-(2-aryl-2-hydroxyethoxy)salicylates and analogs as drugs. EP 514264 A1 921119; Spruce, Lyle W.; Gale, Jonathan B.; Berlin, K. Darrell; Verma, A. K.; Breitman, Theodore R.; Ji, Xinhua; Van der Helm, Dick, Novel heteroarotinoids: synthesis and biological activity. J. Med. Chem. (1991), 34(1), 430–9; Kagechika, Hiroyuki; Kawachi, Emiko; Hashimoto, Yuichi; Shudo, Koichi, Retinobenzoic acids. 2. Structure-activity relationships of chalcone-4-carboxylic acids and flavone-4'-carboxylic acids. J. Med. Chem. (1989), 32(4), 834–40; Shuto, Koichi, Preparation of benzopyran and benzothiopyran derivatives as antitumor agents. JP 62053981 A2 870309 Showa; Waugh, Kristy M.; Berlin, K. Darrell; Ford, Warren T.; Holt, Elizabeth M.; Carrol, John P.; Schomber, Paul R.; Thompson, M. Daniel; Schiff, Leonard J., Synthesis and characterization of selected heteroarotinoids. Pharmacological activity as assessed in vitamin A deficient hamster tracheal organ cultures. Single-crystal x-ray diffraction analysis of 4,4-dimethylthiochroman-6-yl methyl ketone 1,1-dioxide and ethyl (E)-p-[2-(4,4-dimethylthiochroman-6-yl)propenyl]benzoate. J. Med. Chem. 1985), 28(1), 116–24; Chandraratna, Roshantha A. S., Preparation of (chromanylethynyl)heterocyclyl-carboxylates having retinoid-like activity. U.S. Pat. No. 5,089,509 A 920218; Chandraratna, Roshanta A. S., Preparation of 6-(arylalkynyl)benzo(thio)pyrans as retinoate analogs. EP 419132 A2 910327; Berlin, Kenneth D.; Ford, Warren T.; Rajadhyaksha, Shirish N.; Gale, Jonathan B.; Spruce, Lyle W., Preparation of hateroaryl ratinoid analogs as anticancer agents. U.S. Pat. No. 4,977,276 A 901211; Berlin, Kenneth D.; Ford, Warren T.; Raiadhyaksha, Shirish N.; Gale, Jonathan B.; Spruce, Lyle W., Anticancer heteroarotinoids. U.S. Pat. No. 4,833,254 A 890523; Berlin, Kenneth D.; Holt, Elizabeth M.; Ford, Warren T.; Thompson, Mark D., Heteroarotinoid compounds as anticancer agents. U.S. Pat. No. 4,826,984 A 890502; Chandraratna, Roshantha A. S., (Thiochromanylethynyl)- and (chromanylethynyl)benzoic acid derivatives as retinoic acid-like drugs, their preparation, and formulations containing them. EP 290130 A1 881109; Chandraratna, Roshantha A. S., Preparation of disubstituted acetylenes bearing heteroaromatic and heterobicyclic groups having retinoid-like activity. EP 284288 A1 880928; Klaus, Michael; Loeliger, Peter, Preparation and formulation of (phenylpropenyl)heterocycles usefulas neoplasm inhibitors and for treatment of dermatoses. U.S. Pat. No. 4,678,793 A 870707; Spruce, Lyle W.; Rajadhyaksha, Shirish N.; Berlin, K. Darrell; Gale, Jonathan B.; Miranda, Edgar T.; Ford, Warren T.; Blossey, Erich C.; Verma, A. K.; Hossein, M. B.; et al., Heteroarotinoids. Synthesis, characterization, and biological activity in terms of an assessment of these systems to inhibit the induction of ornithine decarboxylase activity and to induce terminal differentiation of HL-60 cells J. Med. Chem. (1987), 30(8), 1474–82; Shuto, Koichi, Preparation of benzopyran and benzothiopyran derivatives as antitumor agents. JP 62053981 A2 870309 Showa; Chan, Rebecca Leung Shun; Chan, Rebecca Leung-shun; Hobbs, Peter D., Benzonorbornenyl-, benzopyranyl- and benzothiopyranylretinoic acid analogs. WO 8500806 A1 850228; Waugh, Kristy M.; Berlin, K. Darrell; Ford, Warren T.; Holt, Elizabeth M.; Carrol, John P.; Schomber, Paul R.; Thompson, M. Daniel; Schiff, Leonard J., Synthesis and characterization of selected heteroarotinoids. Pharmacological activity as assessed in vitamin A deficient hamster tracheal organ cultures. Single-crystal x-ray diffraction analysis of 4,4-dimethylthiochroman-6-yl methyl ketone 1,1-dioxide and ethyl IE)-p-12-(4,4-dimethylthiochroman-6-yl)propenyllbenzoate. J. Med. Chem. (1985), 28(1), 116–24; Dawson, Marcia I.; Hobbs, Peter D.; Derdzinski, Krzysztof; Chan, Rebecca L. S.; Gruber, John; Chao, Wanru; Smith, Saundra; Thies, Richard W.; Schiff, Leonard J.. Conformationally restricted retinoids. J. Med. Chem. (1984), 27(11), 1516–31; Klaus, Michael; Loeliger, Peter. Heterocyclic compounds. DE 3316932 Al 831117; Dauksas, V.; Gaidelis, P.; Petrauskas, O.; Udrenaite, E.; Gasperaviciene, G.; Raguotiene, N., Synthesis and antiinflammatory activity of acyl-substituted benzoxa-and benzodioxaheterocycles and their acyclic analogs. Khim.-Farm. Zh. (1987), 21(5), 569–73; Dauksas, V.; Gaidelis, P.; Udrenaite, E.; Petrauskas, O.; Brukstus, A., Synthesis and antiinflammatory activity of 6-acyl substituted benzo-1,4-dioxanes and chromans. Khim.-Farm. Zh. (1985), 19(9), 1069–71; Yoshimura, Hiroyuki; Nagai, Mitsuo; Hibi, Shigeki; Kikuchi, Koichi; Hishinuma, Ieharu; Nagakawa. Junichi; Asada, Makoto; Miyamoto, Norimasa; Hida, Takayuki; et al., Heterocyclic carboxylic acid derivatives which bind to retinoid receptors (RAR). WO 9414777 Al 940707; Chandraratna, Roshantha A. S., Preparation of phenyl chromancarboxylates and analogs having retinoid activity. U.S. Pat. No. 5,006,550 A 910409; Chandraratna, Roshantha A. S. Preparation of acetylenes disubstituted with a phenyl group and a 2-substituted chromanyl or thiochromanyl group having retinoid-like activity. U.S. Pat. No. 4,980,369 A 901225; Chandraratna, Roshantha A. S., Preparation of phenyl chromancarboxylates and analogs havingretinoid activity. U.S. Pat. No. 5,006,550 A 910409; Berlin, Kenneth D.; Holt, Elizabeth M.; Ford, Warren T.; Thompson, Mark D., Heteroarotinoid compounds as anticancer agents. U.S. Pat. No. 4,826,984 A 890502; Lang, Gerard; Solladie, Guy:

Forestier, Serge; Lagrange, Alain, Preparation of new chroman and thiochroman derivatives useful in cosmetics and medicinal compositions. GB 2188634 A1 871007; Shroot, Braham; Eustache, Jaques; Bernardon, Jean Michel, Arylbenzazoles and their oxygen and sulfur analogs. DE 3533308 A1 860327; other compounds in this class have use as intermediates in the preparation of insecticides: Sugizaki, Hiroyasu; Totani, Tetsuya; Yanagi, Mikio, Method for preparation of chromancarboxylic acid derivative. JP 07010866 A2 950113 Heisei; Sugizaki, Hiroyasu; Totani, Tetsuya; Yanagi, Mikio, Acetophenone derivative and method for its preparation. JP 06329661 A2 941129 Heisei; Sugizaki, Hiroyasu; Totani, Tetsuya; Yanagi, Mikio, Novel benzoic acid derivative and method for its preparation. JP 06329660 A2 941129 Heisei.

It is an object of the subject invention to provide novel compounds which have effective anti-inflammatory and/or analgesic activity.

It is a further object of the subject invention to provide such novel compounds which cause few adverse side effects.

It is also an object of the subject invention to provide methods for treating inflammation andlor pain using the subject novel compounds.

SUMMARY OF THE INVENTION

The subject invention compounds having the structure:

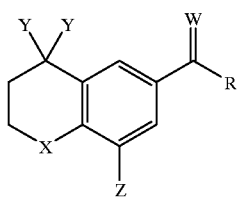

wherein
(a) X is selected from the group consisting of O,S, SO, or $SO_2$;
(b) each Y is independently hydrogen or straight, branched or cyclic alkanyl having from 1 to about 4 carbon atoms, or the two Y's are bonded to form an alkanyl ring having from 3 to about 7 carbon atoms;
(c) Z is branched or cyclic alkyl having from 3 to about 10 atoms other than hydrogen;
(d) W is O or S; and
(e) R is straight, branched or cyclic alkyl or aryl, saturated or mono- or di-unsaturated with double or triple bonds; R having from 1 to about 15 atoms other than hydrogen.

DETAILED DESCRIPTION OF THE INVENTION

As used herein, unless otherwise indicated, "alkyl" and "alkanyl" means a straight, branched or cyclic hydrocarbon chain, saturated or unsaturated, unsubstituted or substituted. Preferred alkyl are straight chain. Preferred branched alkyl have one or two branches, preferably one branch. Preferred cyclic alkyl are monocyclic or are straight chain and monocyclic combination, especially a straight chain with a monocyclic terminus. Preferred alkyl are saturated. Unsaturated alkyl have one or more double bonds or/and one or more triple bonds. Preferred unsaturated alkyl have one or two double bonds or one triple bond, more preferably one double bond. Preferred alkyl are unsubstituted. Preferred substituted alkyl are mono-, di-, or trisubstituted, more preferably monosubstituted. Preferred alkyl substituents include halo, hydroxy, oxo, alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), aryl (e.g., phenyl, tolyl, alkyloxphenyl, alkyloxycarbonylphenyl, halophenyl), heterocyclyl, heteroaryl, amino (e.g., amino, mono- and di- $C_1$–$C_3$ alkanylamino, methylphenylamino, methylbenzylamino) $C_1$–$C_3$ alkanylamido, carbamramido, ureido, N'-alkylureido, N'N'-dialkylureido, N'N'N-trialkylureido, guanidino, N'-alkylguanidino, N',N'',-dialkylguanidiniono or alkoxy carbonyl. Preferred alkyls also include alkyls having heteroatoms selected from the group consisting of oxygen, sulfur, nitrogen and combinations thereof.

As used herein, "alkanyl" means a saturated alkyl.

As used herein, "alkoxy" means —O-alkyl.

As used herein, "terminal carbon atom" means a carbon atom in an alkyl chain which is bonded to only one non-hydrogen atom; "non-terminal carbon atom" means a carbon atom in an alkyl chain bonded to two or more non-hydrogen atoms.

As used herein, "aryl" means a moiety having an unsubstituted or substituted aromatic ring having 6 to about 10 carbon atoms. Preferred aryl are phenyl and naphthyl; most preferred aryl is phenyl. Preferred aryl are unsubstituted. Preferred substituted aryl are mono-, di-, or trisubstituted, more preferably monosubstituted. Preferred aryl substituents include alkyl, alkoxy, hydroxy, thiol, amino, halo. Preferred alkyl substituents are methyl, ethyl and propyl.

As used herein, "heterocyclyl" means a moiety having a saturated or unsaturated non-aromatic ring having from 3 to about 8 ring atoms, including from 2 to about 6 carbon atoms and from 1 to about 4 heteroatoms selected from O, S, and N. Preferred heterocycles are saturated. Preferred heterocycles have 5 or 6 atoms in the ring including 1 or 2 heteroatoms in the ring, also preferably 1 heteroatom in the ring. Specific preferred heterocycles include piperidinyl, tetrahydrothienyl, pyrrolidinyl, piperazinyl, morpholinyl, tetrahydropyranyl, tetrahydrofuranyl, imidazolidinyl, pyrazolidinyl, oxazolidinyl, isoxazolidinyl, oxathiazolidinyl, isothiazolidinyl, azepinyl, oxepinyl, triazolidinyl. Heterocycles are unsubstituted or substituted, preferably unsubstituted. Preferred substituted heterocycles are mono-, di-, or trisubstitued, more preferably monosubstituted. Preferred heterocycle substitutents include alkyl, halo, hydroxy, alkoxy, thio, amino, amido, ureido, guanidino, thiocarbamamido, thioureido.

As used herein, "heteroaryl"0 means a moiety having an aromatic ring having 5 or 6 ring atoms including from 1 to 5 carbon atoms and from 1 to 4 heteroatoms selected from O, S and N. Preferred heteroaryls have 1 or 2 heteroatoms in the ring, also preferably 1 heteroatom in the ring. Specific preferred heteroaryls include pyrrolyl, imidazolyl, pyridyl, pyrimidinyl, pyrazinyl, oxazolyl, isoxazolyl, pyranyl, thienyl, tetrazolyl, thiazolyl, isothiazolyl, furyl, oxathiazolyl. Heteroaryls are unsubstituted or substituted, preferably unsubstituted. Preferred substituted heteroaryls are mono-, di-, or trisubstituted, more preferably monosubstituted. Preferred heteroaryl substituents include alkyl, halo, hydroxy. alkoxy, thio, amino, amido, ureido, guanidino, thiocarbamamido, thiouredio.

As used herein, "halo" means fluoro. chloro, bromo or iodo. Preferred halo are fluoro, chloro and bromo; more preferred are chloro and bromo, especially chloro.

The subject invention involves compounds having the following structure:

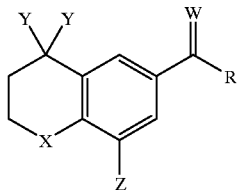

In the above structure, X is O, S, SO, or $SO_2$. Preferred X is O or S, most preferably X is O.

In the above structure, each Y is independently selected from hydrogen, or straight, branched or cyclic alkanyl having from 1 to about 4 carbon atoms, or the Y's are bonded together to form a cyclic alkanyl ring having from 3 to about 7 carbon atoms in the ring. Each Y is preferably hydrogen, methyl, ethyl or cyclopropyl; more preferably hydrogen or methyl; most preferably methyl. When the Y's are bonded together to form a cyclic ring, the ring is preferably cyclopropyl, cyclobutyl or cyclopentyl, more preferably cyclopropyl.

In the above structure, Z is selected from the group consisting of branched or cyclic alkyl having from 3 to about 10 atoms other than hydrogen. Z is preferably branched alkanyl having from about 4 to about 8 carbon atoms, more preferably from about 4 to about 6 carbon atoms. Z is preferably branched alkanyl having 2 or more branches, more preferably 2 branches. Preferred branched alkanyl Z include t-butyl, isopropyl, neopentyl; most preferred is t-butyl. Preferred cyclic alkanyl Z include cyclopropyl, cyclobutyl, cyclopentyl, cyclohexyl, cycloheptyl; most preferred is cyclopentyl.

In the above structure, W is O ro S.

In the above structure, R is straight, branched or cyclic alkyl or aryl, saturated or mono- or di-unsaturated with double bonds; R having from 1 to about 15 atoms other than hydrogen. Preferred R have from about 2 to about 9 atoms other than hydrogen; more preferred R have from about 3 to about 7 atoms other than hydrogen. Preferred substitutents for alkyl R include hydroxy, thiol, amino, halo, phenyl, carboxy, heterocycle and heteroaryl; more preferred include hydroxy, thiol, halo, and heterocycle; more preferred still are hydroxy and chloro.

Preferred straight chain alkyl R are alkanyl, including methyl, ethyl, n-propyl and n-butyl. Preferred straight chain alkanyl R are unsubstituted or substituted; if substituted, they are preferably monosubstituted with hydroxy or halo, especially chioro.

Preferred branched chain alkyl R are alkanyl, preferably having a single alkanyl branch, more preferably a single methyl branch. Preferred branched chain alkanyl R are unsubstituted or substituted; if substituted, they are preferably monosubstituted with hydroxy or halo, especially chloro.

Preferred cyclic alkyl R are alkanyl, preferably cyclopropyl, cyclobutyl or cyclopentyl, or $C_1$ to about $C_4$ straight chain alkanyl with a terminal cyclopropyl, cyclobutyl or cyclopentyl, preferably cyclopropyl. Preferred cyclic alkanyl R are unsubstituted.

Preferred unsaturated alkyl R have the double bond preferably being between the carbon atom bonded to the carbonyl carbon atom and an adjacent non-terminal carbon atom. Preferred unsaturated alkyl R are unsubstituted. Preferred unsaturated alkyl R are straight chain or branched chain with a single branch, preferably a single methyl branch.

Preferred cyclic aryl R are phenyl or naphthyl, preferably phenyl. Preferred cyclic aryl R are unsubstituted.

Preferred compounds of the subject invention include those having the above structure where W is O and with X, R the two Y's, and Z as indicated in the following table:

| Compound No. | R | X | Y | Z |
|---|---|---|---|---|
| 1 | butyl | O | methyl, methyl | t-butyl |
| 2 | 3-cyclopropylpropyl | O | methyl, methyl | t-butyl |
| 3 | 2-hydroxy-2-methylpropyl | O | methyl, methyl | t-butyl |
| 4 | 2-hydroxy-2-methylpropyl | O | H, H | t-butyl |
| 5 | 2-methyl-1-propenyl | O | H, H | t-butyl |
| 6 | 2-chloro-2-methylpropyl | O | H, H | t-butyl |
| 7 | butyl | S | methyl, methyl | t-butyl |
| 8 | 3-tetrahydrofuryl | S | methyl, methyl | t-butyl |

In order to determine and assess pharmacological activity, testing of the subject compounds in animals is carried out using various assays known to those skilled in the art. The anti-inflammatory activity of the subject compounds can be conveniently demonstrated using an assay designed to test the ability of the subject compounds to antagonize the local edema which is characteristic of the inflammatory response. Examples of such known tests include the rat carrageenan edema test, the oxazolone-induced inflamed mouse ear test, and the mouse arachadonic acid-induced inflamed ear test. Analgesic activity may be tested in art-known models such as the phenylbenzoquinone-induced writhing test in mice, and the Randall & Selitto test in rats. Another useful art-known test is the rat adjuvant arthritis test which is a useful model for assessing anti-inflammatory activity, anti-arthritic and anti-resorptive activity in a chronic, rather than an acute, model.

These and other appropriate tests for pharmacological activity are disclosed and/or referred to in U.S. Pat. No. 4,130,666 issued to Moore on Dec. 19, 1978; U.S. Pat. No. 4,431,656 issued Feb. 14, 1984 to Katsumi, et al.; U.S. Pat. No. 4,440,784 issued to Katsumi, et al. on Apr. 3, 1984; Japanese Patent Application 85/54315 of Katsumi, et al., published Mar. 28, 1985; European Patent Application No. 0,059,090 of Yamanuchi Pharmaceutical Company Ltd., published Sep. 1, 1982; Opas, E.V., R. J. Bonney & J. L. Humes, "Prostagiandin and Leukotriene Synthesis in Mouse Ears Inflamed by Arachadonic Acid", *The Journal of Investigative Dermatology*, Vol. 84, No. 4 (1985), pp. 253–256; Swingle, K. F., R. L. Bell & G. G. I. Moore, "Anti-inflammatory Activity of Antioxidants", *Anti-inflammatory and Antirheumatic Drugs*, Vol. III, Chapter 4, K. D. Rainsford, ed., CRC Press, Inc., (1985), pp. 105–126; Adamkiewicz, V. W., W. B. Rice & J. D. McColl, "Antiphlogistic Effect of Trypsin in Normal and in Adrenalectomized Rats", *Canadian Journal of Biochemistry & Physiology*, Vol. 33 (1955), pp. 332–339; Sellye, H., "Further Studies Concerning the Participation of the Adrenal Cortex in the Pathogenesis of Arthritis", *British Medical Journal*, Vol. 2 (1949), pp. 1129–1135; and Winter, C. A., E. A. Risley & G. W. Nuss, "Carrageenan-Induced Edema in Hind Paw of the Rats as an Assay for Antiinflammatory Drugs" *Proceedings of Society of Experimental Biology and Medicine*, Vol. 111 (1962), pp. 544–547; Otterness, I., & M. L. Bliven, "Laboratory Methods for Testing Nonsteroidal Antiinflammatory Drugs", *Nonsteroidal Antiinflammatory Drugs*, Chapter 3, J. G. Lombardino, ed., John Wiley & Sons, Inc. (1985), pp. 111–252. Hitchens, J. T., S. Goldstein, L. Shemano & J. M. Beiler. "Analgesic Effects of Irritants in Three Models of Experimentally-induced Pain". *Arch. Int. Pharmacodyn.*, Vol. 169, No. 2 (1967) pp. 384–393; Milne, G. M. & T. M. Twomey, "The Analgetic Properties of Piroxicam in Animals and Correlation with Experimentally Determined Plasma Levels", *Agents and Actions*, Vol. 10, No. 112 (1980), pp. 31–37; Randall, L. O. & J. J. Selitto, "A Method for Measurement of Analgesic Activity on Inflamed Tissue", *Arch. Int. Pharmacodyn.*, Vol. 111, No. 4 (1957), pp. 409–419; Winter, C. A. & L. Faltaker, "Nociceptive Thresholds as Affected by Parenteral Administration of Irritants and of Various Antinociceptive Drugs", *J. Pharmacol. Exp. Ther.*, Vol. 148, No. 3 (1965), pp. 373–379; the disclosure of all these references are incorporated herein by reference.

Many anti-inflammatory drugs, particularly non-steroidal anti-inflammatory drugs (NSAIDs) cause undesirable gastrointestinal side effects, especially when dosed perorally; such side effects may include ulcers and erosions. These side effects, which are often asymptomatic, can become serious enough to require hospitalization and can even be lethal. Compounds of the subject invention generally cause fewer such gastrointestinal side effects compared to other NSAIDs. Some compounds of the subject invention are even gastroprotective, protecting the stomach and intestines from ulcers and erosions, particularly those caused by ethanol or other NSAIDs.

Certain NSAIDs, when dosed systematically, cause an undesirable increase in systemic levels of certain liver enzymes. Compounds of the subject invention generally cause little or no liver enzyme side effects.

Compounds useful in the subject invention can be made using the following general reaction scheme:

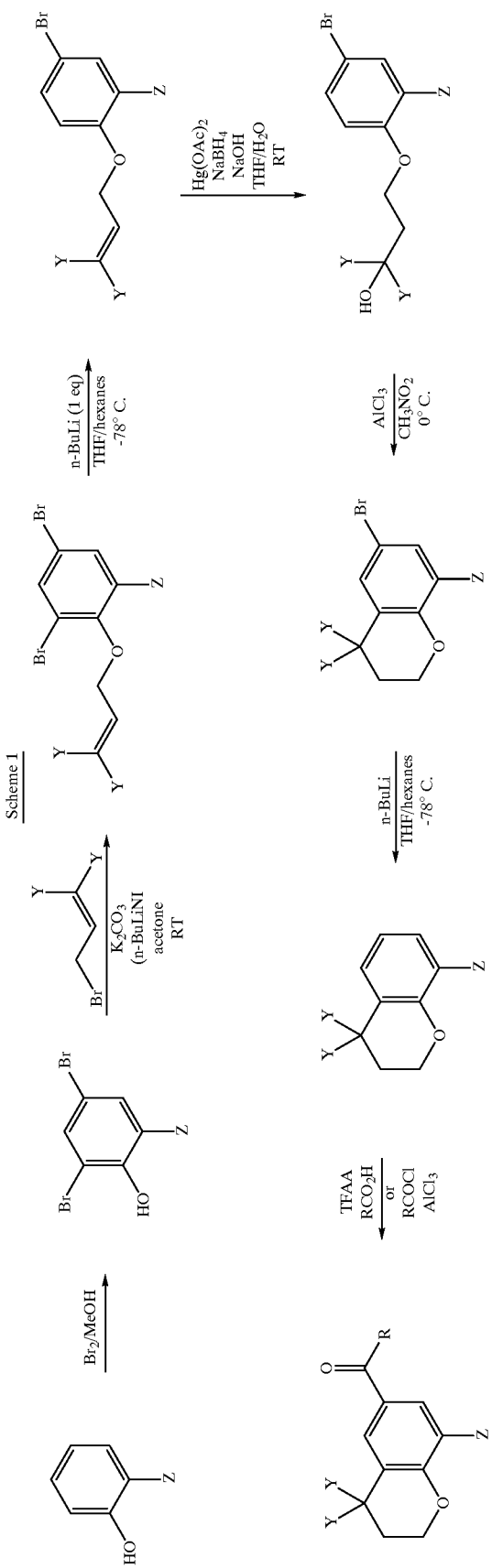
Scheme 1

In Scheme 1, R, Y, and Z are as defined above. The substituted phenols depicted as starting materials in Scheme 1 are either known, commercially available, or readily prepared by methods known to one of ordinary skill in the art. Bromination of such phenol starting materials can be carried out as depicted in Scheme 1. For example, 2,4-dibromo-6-tert-butylphenol is obtained by reaction of 2-tert-butylphenol with bromine in MeOH.

Allylation of such brominated substituted phenols with an allylic halide is depicted in step 2 of Scheme 1. Allylic halides such as 4-bromo-2-methyl-2-butane, 5-bromo-3-ethyl-3-pentene, or cyclpentylidine methyl chloride are reacted with appropriate brominated substituted phenols using reaction conditions readily apparent to a skilled organic chemist. For example, 4-bromo-2-methyl-2-butene reacts with the substituted phenol in the presence of potassium carbonate and catalytic tetra-n-butyl ammonium iodide in acetone to provide the corresponding allylated compounds.

The allylated compounds are cyclized to the dihydrobenzopyrans via the intermediacy of the corresponding alcohols. After lithium halogen exchange of the 2-bromo group followed by protic work-up, oxymercuration with murcuric acetate and sodium borohydride affords the corresponding alcohols. Closure of the alcohols to the dihydrobenzopyrans can be affected with a variety of Lewis acids. The use of aluminum chloride in nitromethane is depicted above. Removal of the remaining bromo substituent can be done by methods known in the art such as hydrogenolysis over inorganic catalysts such as palladium on carbon or by lithium halogen exchange followed by quenching with a proton source such as water.

Compounds of the subject invention are prepared from the fused-ring compounds provided by one of several methods. Acylation of such fused-ring compounds with an appropriate carboxylic acid as depicted can be achieved under reaction conditions readily apparent to one skilled in the art. For example, this reaction can be performed neat or in an inert halogenated solvent, such as $CH_2Cl_2$ using an activating agent such as trifluoroacetic acid anhydride at the appropriate temperature. Alternatively, the same transformation can be accomplished using an acid chloride, derived from the appropriate organic carboxylic acid by well known methods, and a Lewis acid catalyst such as aluminum chloride. In general, the appropriate organic carboxylic acids needed for this reaction are known, commercially available, or readily prepared by those of ordinary skill in the art.

Scheme 2

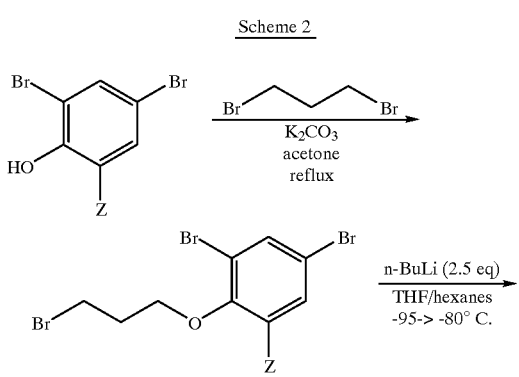

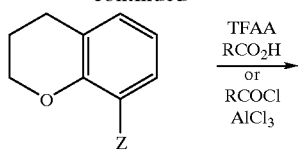

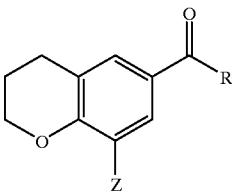

Scheme 2 outlines the synthesis of those compounds where Y=H. The same di-bromophenols shown in Scheme 1 are used as starting materials. Alkylation with 1,3-dibromopropane provides the tribromo ether. Ring closure and removal of the 4-bromo group are accomplished in a single step using excess butyllithium. The acylation step is accomplished in the same way as outline above in Scheme 1.

Scheme 3

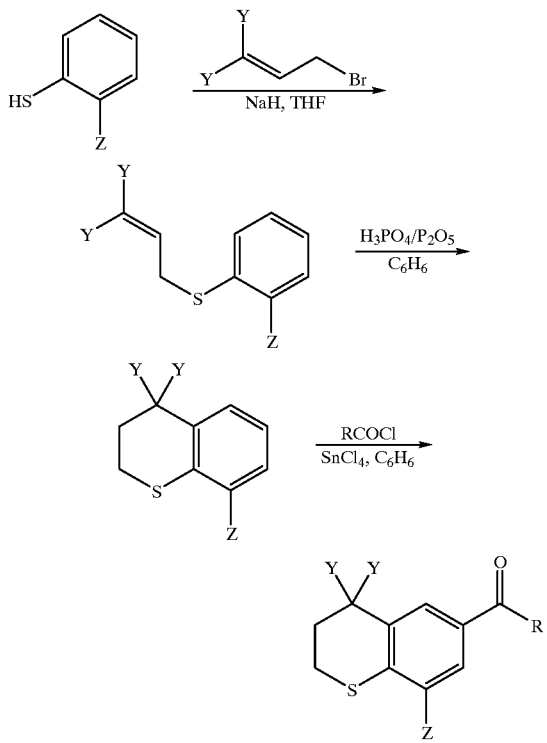

Scheme 3 outlines the synthesis of thiochromanes with a Z group at the 8 position. The starting substituted thiophenol is alkylated with 4-bromo-2-methyl-2-butene and the resulting thioether is ring closed with phosphoric acid and phosphorous pentoxide. The substituted thiochromane is acylated by usual methods, for example, by reaction with an acid chloride and tin tetrachloride.

The following non-limiting examples provide further information regarding synthesis of the subject compounds.

EXAMPLE 1

1-(8-tert-Butyl-4,4-dimethyl-2,3-dihydrobenzopyran-6-yl)-1-pentanone 2,4-dibromo-6-tert-butylphenol.

In a 2 L 3-neck flask, equipped with Ar inlet, reflux condenser, addition funnel, and efficient magnetic stir bar, is placed 2-tert-butylphenol (150.2 g, 1.00 mol) and MeOH (300 mL). The stirred solution is cooled in an ice bath as neat $Br_2$ (321.6 g, 2.01 mol, 2.01 eq) is added dropwise over 0.5 h (Caution: this reaction is exothermic. Control with rate of addition.) The reaction is monitored by TLC (2% EtOAc/hexane), and is complete after 2 h. The reaction mixture is transferred to a 1 L beaker, along with a 20-mL rinse of the reaction flask. The red solution solidifies rapidly to a bright orange crystalline mass. The crystalline mass is redissolved by heating over a steam bath, and then a solution of $Na_2S_2O_5$(1.45 g, 5.4 mmol) in 40 mL $H_2O$ is added, followed immediately by fresh MeOH (60 mL). The resulting suspension is reheated on the steam bath for 10 min (the mixture does not redissolve), and then is vigorously stirred while allowing to cool to room temperature. After 0.5 h, practically all yellow color has vanished, and faint orange-white crystals are deposited. These are filtered and air dried to yield the title compound as faint orange-white platelets.

2,4-Dibromo-6-tert-butyl-1-(2-butenyloxy-3-methyl) benzene.

To a solution of 2,4-dibromo-6-tert-butylphenol (10.00 g, 32.5 mmol) in ethanol (50 mL) is added $K_2CO_3$ (6.73 g, 48.7 mmol, 1.5 equiv), a catalytic amount of n-$Bu_4$NI and 4-bromo-2-methyl-2-butene (5.80 mL, 39.0 mmol, 1.2 equiv). The resulting suspension is stirred at room temperature for 48 h, filtered and concentrated. The residue is purified by flash column chromatography on silica (hexanes) to give the title compound (12.40 g, 100%) as an oil.

4-Bromo-2-tert-butyl-1-(2-butenyloxy-3-methyl) benzene.

To a cold (−78° C.) solution of 2,4dibromo-6-tert-butyl-1-(3-methyl-2-butenyloxy)benzene (12.47 g, 33.15 mmol) in THF/hexanes (100 mL/ 25 mL) is added n-BuLi (13.3 mL, 2.5M/hexanes, 33.15 mmol, 1.0 equiv) dropwise. The resulting pale yellow solution is stirred at −78° C. for 15 min and quenched by slow addition of water, diluted with hexanes, and washed with water followed by brine. The aqueous layers are extracted with hexanes; the combined organic layers are dried ($MgSO_4$), filtered and concentrated. The residue is purified by flash column chromatography on silica (hexanes) to give the title compound (9.35 g, 95%) as an oil.

4-Bromo-2-tert-butyl-1-(3-hydroxy-3-methylbutoxy) benzene.

To a yellow suspension of Hg(OAc)$_2$ (6.36 g, 19.94 mmol, 1.0 equiv) in THF/water (25 mL/ 30 mL) is added 4-bromo-2-tert-butyl-1-(3-methyl-2-butenyloxy)benzene (5.93 g, 19.94 mmol) in THF (5 mL) dropwise and stirred at room temperature for 4 h. To the resulting pale yellow solution is added NaOH (15 mL, 3M) followed by NaBH$_4$ (0.75 g, 19.94 mmol, 1.0 equiv) in NaOH (5 mL, 3M). The resulting ash colored suspension is stirred at room temperature for 30 min, diluted with hexanes, and washed with water, saturated aq. NH$_4$Cl and brine. The aqueous layers are extracted with hexanes; the combined organic layers are dried (MgSO$_4$), filtered and concentrated. The residue is purified by flash column chromatography on silica (hexanes/EtOAc; 101–>311) to give the title compound (4.21 g, 67%) as an oil.

6-Bromo-8-tert-butyl-4,4-dimethyl-2,3-dihydrobenzopyran.

To a cold (0° C.) suspension of AlCl$_3$(1.67 g, 12.51 mmol, 1 equiv) in nitromethane (20 mL) is added a solution of 4-bromo-2-tert-butyl-1-(3-hydroxy-3-methylbutoxy) benzene (3.94 g, 12.51 mmol) in nitromethane (5 mL). The resulting red solution is stirred at 0° C. After 1 h, the reaction mixture is quenched by slow addition of water, diluted with hexanes, and washed with water and brine. The aqueous layers are extracted with hexanes; the combined organic layers are dried (MgSO$_4$), filtered and concentrated. The residue is purified by flash column chromatography on silica (hexanes) to give the title compound (2.87 g, 77%) as a solid which is recrystallized using hexanes to give white crystals.

8-tert-Butyl-4.4-dimethyl-2,3-dihydrobenzotyran.

To a cold (−78° C.) solution of 6-bromo-8-tert-butyl-4,4-dimethyl-2,3-dihydrobenzopyran (2.29 g, 7.72 mmol) in THF/hexanes (28 mL/ 7 mL) is added n-BuLi (3.70 mL, 2.5M/hexanes, 9.26 mmol, 1.2 equiv) dropwise. The resulting pale yellow solution is stirred for 30 min at −78° C. and quenched by slow addition of water, diluted with hexanes, and washed with 1N HCl, water and brine. The aqueous layers are extracted with hexanes; the combined organic layers are dried (MgSO$_4$), filtered and concentrated. The residue is purified by flash column chromatography on silica (hexanes) to give the title compound (1.60 g, 95%) as a solid which is recrystallized using hexanes to afford white crystals.

1-(8-tert-Butyl-4,4dimethyl-2,3-dihydrobenzonyran-6-yl)-1-ethanone.

To neat 8-tert-Butyl-4,4-dimethyl-2,3-dihydrobenzopyran (0.40 g, 1.83 mmol) is added pentanoic acid (0.20 g, 1.93 mmol, 1.05 equiv) and trifluoroacetic anhydride (0.28 mL, 2.02 mmol, 1.1 equiv). The resulting red solution is stirred at room temperature for 2 h, diluted with hexanes, and washed with water (2×) and brine. The aqueous layers are extracted with hexanes; the combined organic layers are dried (MgSO$_4$), filtered and concentrated. The residue is purified by flash column chromatography on silica (hexanes, hexanes/EtOAc; 20/1) to give an oil which is distilled to give the title compound (0.44 g, 79%) as an oil.

Using substantially the last step of the method of Example 1 (and making suitable substitution for the appropriate carboxylic acid) the following subject compounds of example 2 and 5.

EXAMPLE 2

1 -(8-tert-Butyl-4,4-dimethyl-2,3-dihydrobenzopyran-6-yl)-4cyclopropyl-1-butanone

EXAMPLE 3

1-(8-tert-Butyl-4,4-dimethyl-2,3-dihydrobenzopyran-6-yl)-3-hydroxy-3-methyl-1-butanone 1-(8-tert-Butyl-4,4-dimethyl-2,3-dihydrobenzopyvran-6-yl)- 1-ethanone.

To a suspension of AlCl$_3$ (0.32 g, 2.39 mmol, 1.2 equiv) in CH$_2$Cl$_2$ (6 mL) is added acetyl chloride 0.15 mL, 2.19 mmol, 1.1 equiv). The resulting suspension is stirred at room temperature for 5 min and cooled to −78° C. A solution of 8-tert-butyl-2,3-dihydro-4,4-dimethylbenzopyran (0.44 g, 1.99 mmol) in $CH_2Cl_2$ (2 mL) is added dropwise. After the addition is completed, the reaction mixture is stirred at −78° C. for 2 h and then quenched by slow addition of water at −78° C. The resulting suspension is allowed to warm to room temperature, diluted with hexanes and washed with water (2×) and brine. The aqueous layers are extracted with hexanes; the combined organic layers are dried ($MgSO_4$), filtered and concentrated. The residue is purified by flash column chromatography on silica (hexanes, hexanes/EtOAc; 20/1) to give a solid which is recrystalized using hexanes to give the title compound (0.40 g, 76%) as a white solid.

1-(8-tert-Butyl-4,4-dimethyl-2,3-dihydrobenzopyran-6-yl)-3-hydroxy-3-methyl-1-butanone.

To a cold (−78° C.) solution of 1-(8-tert-butyl-4,4-dimethyl-2,3-dihydrobenzopyran-6-yl)1-ethanone (0.35 g, 1.36 mmol) in $CH_2Cl_2$ (3.0 mL) is added TMSOTf (0.32 mL, 1.63 mmol, 1.2 equiv) and $(i-Pr)_2NEt$ (0.28 mL, 1.63 mmol, 1.2 equiv) dropwise. The resulting red mixture is stirred at −78° C. for 30 min, and then allowed to warm to room temperature over 1 h. The resulting pale red solution is recooled to −78° C. and acetone (0.12 mL, 1.63 mmol, 1.2 equiv) and $TiCl_4$ (0.15 mL, 1.36 mmol, 1.0 equiv) are added dropwise. The resulting deep red solution is allowed to warm to room temperature over 3.5 h and 0.5N HCl is added and the mixture is stirred for 30 min. The reaction mixture is diluted with hexanes and washed with water and brine. The aqueous layers are extracted with hexanes; the combined organic layers are dried ($MgSO_4$), filtered and concentrated. The residue is purified by flash column chromatography on silica (hexanes, hexanes/EtOAc; 10/1) to give the title compound (0.30 g, 70%) as a pale yellow solid which is recrystallized using pentane.

EXAMPLE 4

1-(8-tert-Butyl-2,3-dihydrobenzopyran-6-yl)-3-hydroxy-3-methyl-1-butanone 1-5-Dibromo-2-(3-bromopropyoxy)-3-tert-butylbenzene.

To a pale brown solution of 2,4-dibromo-6-tert-butylphenol (5.00 ga 16.24 mmol) in acetone (70 mL) is added 1,3-dibromopropane (3.30 mL, 32.47 mmol, 2 equiv) and $K_2CO_3$ (6.70 g, 48.72 mmol, 3 equiv) and allowed to reflux. After 14 h, the mixture is filtered, concentrated, the residue is purified by flash column chromatography on silica (hexanes) to give an off-white oil which is Kugelrohr distilled to give the title compound (6.13 g, 88%) as a pale-yellow oil.

8-tert-Butyl-2,3-dihydrobenzopyran.

To a cold (−95° C., MeOH/$Et_2O$, liq $N_2$) solution of 1-5-dibromo-2-(3-bromopropyloxy)-3-tert-butylbenzene (5.00 g, 11.66 mmol) in THF/hexanes (100 mL/20 mL) is added butyllithium (11.60 mL, 29.14 mmol, 2.5 equiv) dropwise and allowed to stir at −95° C. for 30 min and is warmed to −80° C. After 4 h, the reaction mixture is poured into saturated $NH_4Cl$, extracted with EtOAc, and washed with water (2×) and brine. The aqueous layers are extracted with EtOAc and the combined organic layer is dried ($MgSO_4$), filtered and concentrated. The resulting residue is purified by flash column chromatography on silica (hexanes) to give an off-white oil which is Kugelrohr distilled to give the title compound (1.92 g, 87%) as an off-white oil.

1-(8-tert-Butyl-2,3-dihydrobenzopyran-6-yl)-1-ethanone.

To a suspension of $AlCl_3$ (0.54 g, 4.05 mmol, 1.1 equiv) in $CH_2Cl_2$ (20 mL) is added acetyl chloride (0.28 mL, 4.05 mmol, 1.1 equiv). The resulting suspension is allowed to stir at −78° C. for 30 min, and a solution of 8-tert-butyl-2,3-dihydrobenzopyran (0.70 g, 3.68 mmol) in $CH_2Cl_2$ (5 mL) is added dropwise using an addition funnel. After the addition is complete, the reaction mixture (pale yellow precipitate) is allowed to warm to room temperature over 4 h. The resulting suspension is cooled to 0° C and quenched with water, washed with water and brine. The aqueous layers are extracted with $CH_2Cl_2$, the combined organic layer is dried ($MgSO_4$), filtered and concentrated. The resulting off-white solid is recrystallized using hexanes to give the title compound (0.67 g, 79%) as white crystals.

1-(8-tert-Butyl-2,3-dihydrobenzopyran-6-yl)-3-hydroxy-3-methyl-1-butanone.

To a cold (−78° C.) solution of 8-tert-butyl-2,3-dihydrobenzopyran-6-yl)-1-ethanone (0.45 9, 1.93 mmol in $CH_2Cl_2$ (4.0 mL) is added TMSOTf (0.45 mL, 2.31 mmol, 1.20 equiv) and $(i-Pr)_2NEt$ (0.40 mL, 2.31 mmol, 1.2 equiv) dropwise. The resulting pale yellow mixture is stirred at −78° C. for 15 min, and then allowed to warm to room temperature over 1 h. The resulting colorless solution is recooled to −78° C. and acetone (0.17 mL, 2.31 mmol, 1.2 equiv) and $TiCl_4$ (0.21 mL. 1.93 mmol, 1.0 equiv) are added dropwise. The resulting deep red solution is allowed to warm to room temperature over 2 h and 1N HCl is added and the mixture was stirred for 30 min. The reaction mixture is diluted with $CH_2Cl_2$ and washed with water and brine. The aqueous layers are extracted with $CH_2Cl_2$, the combined organic layers are dried ($MgSO_4$), filtered and concentrated. The residue is purified by flash column chromatography on silica (hexanes, hexanes/EtOAc; 10/1, 8/1, 4/1) to give a crude oil which is distilled to give the title compound (0.40, 72%) as a colorless oil.

EXAMPLE 5

1-(8-tert-Butyl-2,3-dihydrobenzopyran-6-yl)-3-methyl-2-buten-1-one

The method of example 1 was used.

EXAMPLE 6

1-(8-tert-Butyl-2,3-dihydrobenzopyran-6-yl)-3-chloro-3-methyl-1-butanone

To a solution of 1-(8-tert-butyl-2,3-dihydrobenzopyran-6-yl)-3-methyl-2-buten-1-one (0.62 g, 2.26 mmol) in $Et_2O$ (10 mL) is bubbled hydrogen chloride gas for about 15 min. The resulting solution is stirred at room temperature for 1 h, and concentrated. The resulting off-white oil is purified by flash column chromatography on silica (hexanes, hexanes/EtOAc; 10/1) to give the title compound (0.425 g. 61 %) as a pale yellow oil.

EXAMPLE 7

8-tert-Butyl-4,4-dimethyl-6-( 1-oxopentyl)-thiochromane 2-tert-Butylphenyl 1-(3'-methylbut-2'-enyl) sulphide:

2 g (69 mmol) of an 80% dispersion of sodium hydride in mineral oil is washed twice with hexane under argon atmosphere. To this is added 20 mL anhydrous tetrahydrofuran. The mixture is cooled to 0° C. Aside, 10 g (60 mmol) 2-tert-butylthiophenol is dissolved in 60 mL tetrahydrofuran. This is added slowly to the sodium hydride mixture. This is allowed to stir 40 minutes at 0° C. A solution of 6.9 mL (60 mmol) 4-bromo-2-methyl-2-butene in 20 mL anyhydrous tetrahydrofuran is then added. This stirs 30 minutes at 0° C. and 15 minutes at room temperature. The reaction is diluted with 500 mL ether and washed with 1M NaOH. The organics are dried over sodium sulfate and concentrated under reduced pressure to give 13.5 g (96% yield) of 2-tert-butylphenyl 1-(3'-methylbut-2'-enyl) sulphide as a tan liquid which is used without further purification.

8-tert-Butyl-4,4-dimethylthiochromane:

11 g (47 mmol) of 2-tert-butylphenyl-1-(3'-methylbut-2'-enyl) sulphide and 8.25 g (71.6 mmol) of 85% $H_3PO_4$ in 110 mL benzene is allowed to stir at reflux for 16 hours. Then, over an 8 hour period, three 5.5 g (116 mmol) portions of $P_2O_5$ are added to the refluxing mixture. The reaction is allowed to stir further at reflux for 16 more hours. The mixture is allowed to cool to room temperature. The solution is decanted off the red residue into a 10% solution of sodium chloride in a separatory funnel. The residue is washed with ether and 10% sodium chloride and both of these washings are added to the separatory funnel. The product is extracted into the benzeneleather layer and this is washed again with salt solution. The organics are dried over sodium sulfate, and concentrated under reduced pressure to give 6.5 g (60% yield) of 8-tert-butyl-4,4-dimethylthiochromane.

8-tert-Butyl-4,4-dimethyl-6-(1-oxopentyl)-thiochromane:

To 500 mg (2.1 mmol) of 8-tert-butyl-4,4-dimethylthiochromane and 0.29 mL (2.34 mmol) of pentlanoyl chloride in 10 mL benzene at 0° C. is added 0.27 mL (2.34 mmol) of tin tetrachloride. The reaction is allowed to stir 1 hour at 0° C. and is then diluted with ether and washed with water and 10% sodium chloride. The product is purified by flash silica gel chromatography, eluting with 7:3 hexane-:ethyl acetate to give 250 mg (37% yield) of the title compound.

EXAMPLE 8

8-tert-Butyl-4,4-dimethyl-6-(1-oxo-1-(3-tetrahydrofuryl)methylthiochromane

To 600 mg (2.56 mmol) of 8-tert-butyl-4,4-dimethyl-thiochromane and 0.38 g (2.84 mmol) of (+/−) tetrahydro-3-furoic acid chloride [which is prepared by reacting 1.5 g (12.9 mmol) (+/−) tetrahydro-3-furoic acid with 1.38 mL (15.5 mmol) oxalyl chloride in 40 mL benzene at 50° C. for 1 hour followed by concentration of the volatiles under reduced pressure] in 10 mL benzene at 0° C. is added 0.32 mL (2.73 mmol) tin tetrachloride. The reaction is allowed to stir 1 hour at 0° C. and is then diluted with ether and washed with water and sodium chloride. The product is purified by flash silica gel chromatography, eluting with 7:3 hexane-:ethyl acetate to give 257 mg of 8-tert-butyl-4,4-dimethyl-6-(1-oxo-1-(3-tetrahydrofuryl)methylthiochromane.

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of the subject invention preferably comprise from about 0.1% to about 99.9% by weight of a compound, more preferably from about 20% to about 80%, and most preferably from about 40% to about 70%.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate: vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweense; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a subject compound is basically determined by the way the compound is to be administered.

If the subject compound is to be injected, it is preferably injected non-intravenously; the preferred pharmaceutically-acceptable carrier is sterile, physiological saline, with blood compatible suspending agent, the pH of which has been adjusted to about 7.4. Such injectable compositions preferably comprise from about 1% to about 50% of the subject compound, more preferably from about 5% to about 25%, also preferably from about 10 mg to about 600 mg of the subject compound per dose.

Suitable pharmaceutically-acceptable carriers for topical application include those suited for use in lotions, creams, gels and the like. Topical compositions preferably contain from about 1 % to about 50% of an emollient, more preferably from about 5% to about 25% of an emollient. Such topical compositions preferably comprise from about 0.1 % to about 50%, of the subject compound, more preferably from about 0.5% to about 10%, also preferably from about 5 mg to about 1000 mg per dose.

The preferred mode of administering the subject compound is perorally. The preferred unit dosage form is therefore tablets, capsules and the like, comprising a safe and effective amount of the compound, which is preferably from about 5 mg to about 3500 mg, more preferably from about 10 mg to about 1000 mg, and most preferably from about 25 mg to about 600 mg.

Many of the subject compounds are hydrophobic. If it is desired to provide an aqueous-based composition or a composition soluble in or miscible with aqueous media, a solubilizing agent may be included in the composition. Non-limiting examples of such solubilizing agents include polyethylene glycol, propylene glycol, ethanol, and polyoxyethylene (35) castor oil.

Particularly preferred oral composition carriers suitable for compositions of the subject invention are disclosed in U.S. Pat. No. 5,189,066 of Kelm & Bruns, issued Feb. 23, 1993, entitled "Pharmaceutical Compositions of Tebufelone", and U.S. Pat. No. 5,281,420 of Kelm & Dobrozsi, issued Jan. 25, 1994, entitled "Solid Dispersion Compositions of Tebufelone", hereby incorporated herein by reference.

Another aspect of the subject invention is methods for treating or preventing diseases characterized by inflammation by administering a safe and effective amount of a subject compound to a human or lower animal in need of such treatment. The term "diseases characterized by inflammation", as used herein, means conditions which are known to involve inflammation, and may include conditions such as arthritis (e.g., rheumatoid arthritis, osteoarthritis, psoriatic arthritis, juvenile arthritis, Reiter's syndrome, infectious arthritis, and ankylosing spondylitis, systemic lupus, erythematosus and gout), as well as the presence of inflammation whether or not it is associated with an identifiable disease. Diseases characterized by inflammation further may include inflammation in the oral cavity (e.g., inflammation associated with gingivitis or periodontal disease); inflammation in the gastrointestinal tract. (e.g., inflammation associated with ulcers and irritable bowel disease); inflammation associated with dermatological diseases (e.g., psoriasis, acne, and other skin inflammation); inflammation associated with the respiratory tract (e.g., asthma, bronchitis, and allergies);. and inflammation in the central nervous system (e.g., Alzheimer's disease).

Another aspect of the subject invention is methods for treating or preventing pain by administering a safe and effective amount of a subject compound to a human or lower animal in need of such treatment. Pain which can be treated or prevented by administering the subject compounds may include peripheral pain, menstrual pain, dental pain, and lower back pain.

Another aspect of the subject invention is methods for preventing oxidative damage at inflammatory sites by administering a safe and effective amount of a subject compound to a human or lower animal in need of such treatment. While not limited to a particular mechanism, it is believed that the subject compounds inhibit leukotriene synthesis, thereby decreasing neutrophil accumulation at an inflammatory site.

Another aspect of the subject invention is methods for treating or preventing gastric or duodenal ulcers or erosions by administering a safe and effective amount of a subject compound to a human or lower animal in need of such treatment. In particular, such ulcers or erosions caused by ethanol or non-steroidal antiinflammatory drugs (NSAIDs) can be treated and/or prevented by administration of preferred subject compounds.

Appropriate tests for determining the gastrointestinal safety or gastroprotective properties of the subject compounds are known.

Methods for determining acute gastrointestinal safety are disclosed and/or referred to in the following references: Unangst, P. C., G. P. Shrum, D. T. Connor, R. D. Dyer, and D. J. Schrier, "Novel 1,2,4-Oxadiazoles and 1,2,4-Thiadiazoles as Dual 5-Lipoxygenase and Cyclooxygenase Inhibitors", J. Med. Chem., Vol. 35 (1992), pp. 3691–3698; and Segawa, Y, O, Ohya, T. Abe, T. Omata, et al., "Anti-inflammatory, Analgesic, and Antipyretic Effects and Gastrointestinal Toxicity of the New Anti-inflammatory Drug N-{3-[3-(piperidinylmethyl)phenoxy] propyl}-carbamoylmethylthiolethyl 1-(p-chlorobenzoyl) 5-Methoxy-2methyl-3-indolylacetate", Arzneim.-Forsch./ Drug Res., Vol. 42 (1992), pp. 954–992. In the methods disclosed therein, stomachs of the animals are typically examined two hours after dosing a compound. Methods for determining subchronic gastrointestinal safety are disclosed and/or referred to in the following references: Melarange, R., C. Gentry, et al., "Anti-inflammatory and Gastrointestinal Effects of Nabumetone or Its Active Metabolite, 6-Methoxy-2-naphthylacetic Acid (6MNA)", Dig. Dis. Sci., Vol. 37 (1992), pp. 1847–1852; and Wong, S., S. J. Lee, et al., "Antiarthritic Profile of BF-389 - A Novel Anti-inflammatory Agent With Low Ulcerogenic Liability", Agents Actions, Vol. 37 (1992), pp. 90–91.

Methods for determining acute gastroprotection are disclosed and/or referred to in the following reference: Playford, R. J., D. A. Versey, S. Haldane, M. R. Alison, and J. Calan, "Dose-dependent Effects of Fentanyl on Indometharin-induced Gastric Damage", Digestion, Vol. 49 (1991), pp. 198–203. In the method disclosed therein, female Lewis rats (130–175 g) are dosed perorally with the subject compound (40 mg/kg b.i.d.) or vehicle at 2 hours and immediately before administration of a gastric damaging dose of indomethacin. The rats are sacrificed 4 hours later by $CO_2$ asphyxiation. Gastric corpus damage (millimeters of hemorrhagic lesions) is measured by digitized imaging.

The preferred mode of administration of the subject compounds is peroral, but other known methods of administration are contemplated as well, e.g., dermatomucosally (for example, dermally, rectally and the like), and parenterally (for example, by subcutaneous injection, intramuscular injection, intraarticular injection, intravenous injection and the like). Ocular administration and inhalation are also included. Thus specific modes of administration include, without limitation, peroral, transdermal, mucosal, sublingual, intranasal, intramuscular, intravenous, intraperitoneal, subcutaneous, and topical administration.

Preferred doses of the subject compounds range from about 0.2 mg/kg to about 70 mg/kg, more preferably from about 0.5 mg/kg to about 12 mg/kg. Preferred injectable doses comprise from about 0.1 mglkg to about 10 mg/kg of the subject compound. Preferred topical doses comprise from about 1 mg/cm² to about 200 mg/cm² of the subject compound applied to the skin surface. Preferred peroral doses comprise from about 0.5 mg/kg to about 50 mg/kg, more preferably from about 1 mg/kg to about 20 mg/kg, more preferably still from about 2 mg/kg to about 10 mg/kg, of the subject compound. Such doses are preferably administered from about once to about six times daily, more preferably from about twice to about four times daily. Such daily doses are preferably administered for at least one week, also preferably for at least two weeks, also preferably at least one month, also preferably for at least 2 months, also preferably for at least 6 months, 1 year, 2 years, or more.

The following non-limiting examples illustrate the subject invention.

EXAMPLE A

A pharmaceutical composition in tablet form is prepared by conventional methods, such as mixing and direct compaction, formulated as follows:

| Ingredient | Quantity (mg per tablet) |
| --- | --- |
| Compound 1 | 200 |
| Microcrystalline Cellulose | 100 |
| Sodium Starch Glycollate | 30 |
| Magnesium Stearate | 3 |

When administered orally two times daily, the above composition significantly reduces the inflammation in a patient suffering from rheumatoid arthritis. A significant benefit is also achieved by twice daily administration of this composition to a patient suffering from osteoarthritis

EXAMPLE B

A pharmaceutical composition in capsule form is prepared by conventional methods, formulated as follows:

| Ingredient | Quantity (mg per tablet) |
| --- | --- |
| Compound 1 | 200 |
| Lactose | To fill to volume of capsule |

The above capsule administered orally once a day substantially reduces the symptoms of a patient afflicted with rheumatoid arthritis or osteoarthritis.

EXAMPLE C

A pharmaceutical composition in liquid form is prepared by conventional methods, formulated as follows:

| Ingredient | Quantity |
| --- | --- |
| Compound 3 | 200 mg |
| EtOH | 4 ml |
| Methyl cellulose | 0.4 mg |
| Distilled water | 76 ml |
| Tween 80 | 1.6 ml |

50 ml of the above composition administered perorally once a day substantially reduces the symptoms of a patient afflicted with rheumatoid arthritis or osteoarthritis.

EXAMPLE D

A pharmaceutical composition in liquid form is prepared by conventional methods, formulated as follows:

| Ingredient | Quantity |
| --- | --- |
| Microcrystalline (micronoized) Compound 4 | 200 mg |
| Avicel (microcrystalline cellulose) | 50 mg |
| Tween 80 | 1.6 ml |
| Methyl cellulose | 0.4 mg |
| Deionized water | 80 ml |

50 ml of the above composition administered perorally twice a day substantially reduces the symptoms of a patient afflicted with rheumatoid arthritis or osteoarthritis.

EXAMPLE E

An oral solid pharmaceutical composition is prepared by conventional methods, formulated as follows:

| Ingredient | Quantity (% by weight) |
| --- | --- |
| Compound 5 | 20 |
| Pluronic F108 | 40 |
| Tween 80 | 40 |

EXAMPLE F

An oral solid pharmaceutical composition is prepared by conventional methods, formulated as follows:

| Ingredient | Quantity (% by weight) |
| --- | --- |
| Compound 6 | 50 |
| Triglycerides and derivatives | 45 |
| Cremaphor EL | 5 |

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

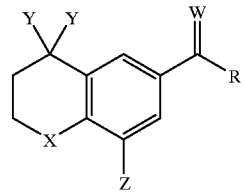

wherein (a) X is selected from the group consisting of O, S, SO and $S_2O$;

(b) each Y is independently selected from hydrogen and methyl;

(c) Z is t-butyl;

(d) W is O; and (e) R is $C_1$–$C_7$ straight or single-branched alkyl or aryl, saturated or unsaturated with one double bond between non-terminal carbon atoms, or $C_3$–$C_6$ cycloalkanyl or aryl; unsubstituted or monosubstituted with a substituent selected from the group consisting of halo, hydroxy, thiol, phenyl, heteroaryl and heterocycle; R having from 1 to about 7 atoms other than hydrogen.

2. The compound of claim 1 wherein R is selected from the group consisting of methyl, ethyl, n-propyl, n-butyl, i-propyl, cyclopropyl, cyclopentyl, 3-cyclopropylpropyl, 2-chloro-2-methylpropyl, 2-hydroxy-2-methylpropyl, 2-methyl-d-propenyl, 3-tetrahydrofuryl.

3. The compound of claim 2 wherein X is oxygen.

4. The compound of claim 3 wherein R is selected from the group consisting of methyl, ethyl, n-propyl, n-butyl, i-propyl, cyclopropyl, cyclopentyl, 3-cyclopropylpropyl, 2-chloro-2-methylpropyl, 2-hydroxy-2-methylpropyl, 2-methyl-2-propenyl, and 2-methyl-1-propenyl.

5. The compound of claim 4 wherein both Y are hydrogen and R is selected from the group consisting of 2-hydroxy-2-methylpropyl, 2-methyl-d-propenyl, and 2-chloro-2-methyl-propyl.

6. The compound of claim 4 wherein both Y are methyl and R is selected from the group consisting of n-butyl, 3-cyclopropylpropyl, and 2-hydroxy-2-methylpropyl.

7. The compound of claim 2 wherein X is sulphur.

8. The compound of claim 7 wherein R is selected from the group consisiting of butyl and 3-tetrahydrofuryl.

9. The compound of claim 8 wherein both Y are methyl and R is 3-tetrahydrofuryl or butyl.

10. A composition comprising a compound of claim 1 and a pharmaceutically-acceptable carrier.

11. A method of treating inflammation or pain comprising administation, to a human or lower animal in need of such treatment, of a safe and effective amount of a compound of claim 1.

12. A method of treating arthritis comprising daily peroral administration, to a human in need of such treatment, of from about 1 mg/kg to about 20 mg/kg of a compound of claim 1.

13. A composition comprising a compound of claim 4 and a pharmaceutically-acceptable carrier.

14. A method of treating inflammation or pain comprising administation, to a human or lower animal in need of such treatment, of a safe and effective amount of a compound of claim 4.

15. A method of treating arthritis comprising daily peroral administration, to a human in need of such treatment, of from about 1 mg/kg to about 20 mg/kg of a compound of claim 4.

16. A composition comprising a compound of claim 8 and a pharmaceutically-acceptable carrier.

17. A method of treating inflammation or pain comprising administation, to a human or lower animal in need of such treatment, of a safe and effective amount of a compoundof claim 8.

18. A method of treating arthritis comprising daily peroral administration, to a human in need of such treatment, of from about 1 mg/kg to about 20 mg/kg of a compound of claim 8.

* * * * *